US008159237B2

United States Patent
(12) United States Patent
Schleicher et al.

(10) Patent No.: US 8,159,237 B2
(45) Date of Patent: Apr. 17, 2012

(54) GRID SENSOR

(75) Inventors: Eckhard Schleicher, Dresden (DE); Tobias Sühnel, Dresden (DE); Frank Fischer, Dresden (DE); Hein Futterschneider, Dürrröhrsdorf (DE); Dieter Boden, Grossröhrsdorf (DE)

(73) Assignee: Helmholtz-Zentrum Dresden-Rossendorf E.V., Dresden (DE)

( * ) Notice: Subject to any disclaimer, the term of this patent is extended or adjusted under 35 U.S.C. 154(b) by 350 days.

(21) Appl. No.: 12/597,842

(22) PCT Filed: Apr. 23, 2008

(86) PCT No.: PCT/DE2008/000694

§ 371 (c)(1), (2), (4) Date: Oct. 27, 2009

(87) PCT Pub. No.: WO2008/131730

PCT Pub. Date: Nov. 6, 2008

(65) Prior Publication Data

US 2010/0117664 A1 May 13, 2010

(30) Foreign Application Priority Data

Apr. 27, 2007 (DE) ......................... 10 2007 019 926

(51) Int. Cl.
*G01R 31/02* (2006.01)
*G01R 27/08* (2006.01)

(52) U.S. Cl. ........................... 324/691; 324/72; 324/714

(58) Field of Classification Search .................... 324/72, 324/72.5, 658, 663, 664, 686, 689–691, 693–696, 324/701, 713, 715, 722, 724

See application file for complete search history.

(56) References Cited

U.S. PATENT DOCUMENTS 4,644,263 A 2/1987 Johnson
5,210,499 A 5/1993 Walsh
6,314,373 B1 * 11/2001 Prasser et al. .................. 702/23

FOREIGN PATENT DOCUMENTS

DE 19649011 A1 5/1998

OTHER PUBLICATIONS

Prasser et al: "Bubble Size Measurement Using Wire-Mesh Sensors", Flow Measurement and Instrumentation Elsevier UK, Aug. 2001, pp. 299-312, XP002491654, vol. 12, No. 4.

* cited by examiner

*Primary Examiner* — Melissa Koval
*Assistant Examiner* — Farhana Hoque
(74) *Attorney, Agent, or Firm* — Laurence A. Greenberg; Werner H. Stemer; Ralph E. Locher

(57) ABSTRACT

A grid sensor significantly reduces the complexity of a production process. The cost for installing and running the grid sensor are significantly reduced and the service life, pressure and heat resistance of the grid sensor can be significantly increased over previous grid sensors. Channels, which are wider than the diameter of the wire electrodes and have a depth of less than half the thickness of the sensor board, run outwardly from the edge of the measurement cross section in the sensor board. The channels are coated by a metal layer and the wire electrodes are inserted into the periphery of the measurement cross section. The two ends of the electrode, each in one of the opposite channels, and the electrodes are fixed in the channels by means of a conductive sealing compound. In each channel, the conductive sealing compound terminates in a planar fashion with the upper side of the sensor board, and the sensor board is clamped between two clamping plates.

6 Claims, 3 Drawing Sheets

2
10
6
11
12
12
10
1

GRID SENSOR

BACKGROUND OF THE INVENTION

Field of the Invention

The invention relates to a grid sensor for measuring the distribution of electrical or non-electrical variables of a medium by means of a two or multi-layer electrode grid. Fields of application are the determination of the liquid distribution and the liquid level in vessels and the examination of gas-liquid two-phase flows, particularly in piping.

Grid sensors are often used for examining two-phase flows and liquid distributions in piping and vessels. U.S. Pat. Nos. 4,644,263, 5,210,499 and DE 19 649 011 describe arrangements by means of which the electrical conductivity can be measured within a measurement cross section using a grid-shaped electrode arrangement and associated electronics. In these arrangements, wire-shaped electrodes in an excitation electrode plane of the grid are successively actuated with a voltage signal and a current signal is detected on the wire electrodes in a receiver electrode plane of the grid arranged parallel to and at a short distance from said excitation electrode plane. As a result of this, these arrangements are able to determine the conductivity between the two planes at the crossing points of the projections of the electrodes (referred to as "crossing points" in the following text) at a very high measurement frequency.

High requirements in respect of the usage conditions are placed on the grid sensors. They are often used in a rough industrial environment in installations with high operational pressures and temperatures and in the process can come into contact with aggressive substances such as acids, bases or other solvents. The production of electrically insulating, pressure and heat resistant passages for the electrodes in the sensor frame which is often designed as a metal pipe segment constitutes a particular problem.

In the case of grid sensors destined for use under pressures of up to 7 MPa and operational temperatures under 120° C., it is common knowledge to attach the sensor electrode grid to a carrier board, usually an electronics printed circuit board made of FR4, by soft soldering. There is a cutout on the board for the flow cross section to be measured. After being equipped, the sensor board is molded between two flange segments by means of a casting resin. After the casting resin has been cured, the sensor can then be installed in piping like a flange or another vessel by being screwed in. The weak point of this grid sensor arrangement and the production technology thereof often is the casting. In the process, current carrying parts of the sensor board (conductor tracks, solder points, electrodes) sometimes come into contact with the metal structures of the frame, the required pressure tightness is absent after curing and/or leakages occur. Remains of the casting compound often enter the measurement cross section, surround the wires and thus render the sensor useless. Casting the complicated grid structure in the sensor frame can hardly be effected automatically and thus requires high production complexity. After casting, correction and repair are no longer possible. Grid sensors for high pressures and temperatures are produced in an even more complex and cost-intensive fashion. Since organic casting resins fail at temperatures above 120° C. and in the presence of water or steam, the sensor wires of such sensors are led over relatively long distances through bores or openings of the sensor metal body, possibly with the use of insulating ceramics, to places at a lower temperature, where pressure tight casting is possible. (DE 10 2005 019 739.6-09). This type of design and production leads to high costs.

BRIEF SUMMARY OF THE INVENTION

It is the object of the present invention to propose a grid sensor by means of which the complexity of the production process and the installation and running costs of the grid sensor are significantly reduced and the service life and pressure and heat resistance of the grid sensor can be significantly increased over previous grid sensors.

According to the invention, this object is achieved by the features of claim 1. Refinements of the invention are detailed in the dependent claims.

BRIEF DESCRIPTION OF THE SEVERAL VIEWS OF THE DRAWING

In the following text, the invention will be explained on the basis of an exemplary embodiment of the grid sensor.

In the associated drawing.

DESCRIPTION OF THE INVENTION

Figure 1:
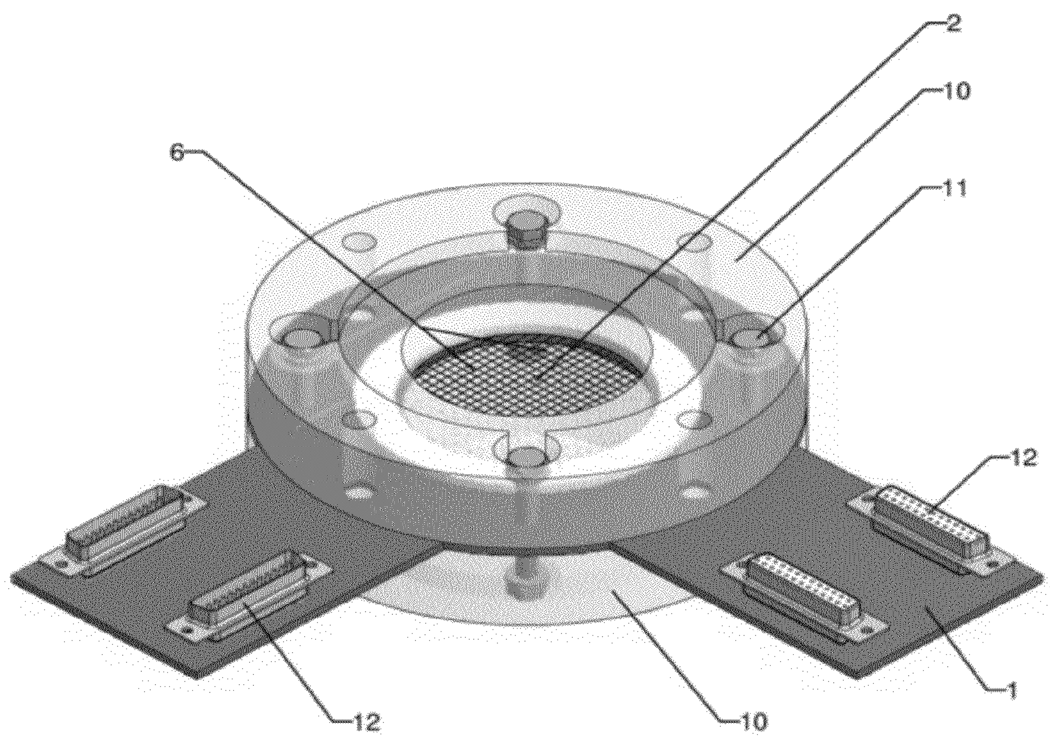
FIG. 1 shows a 3D view of the complete grid sensor.
Figure 2:
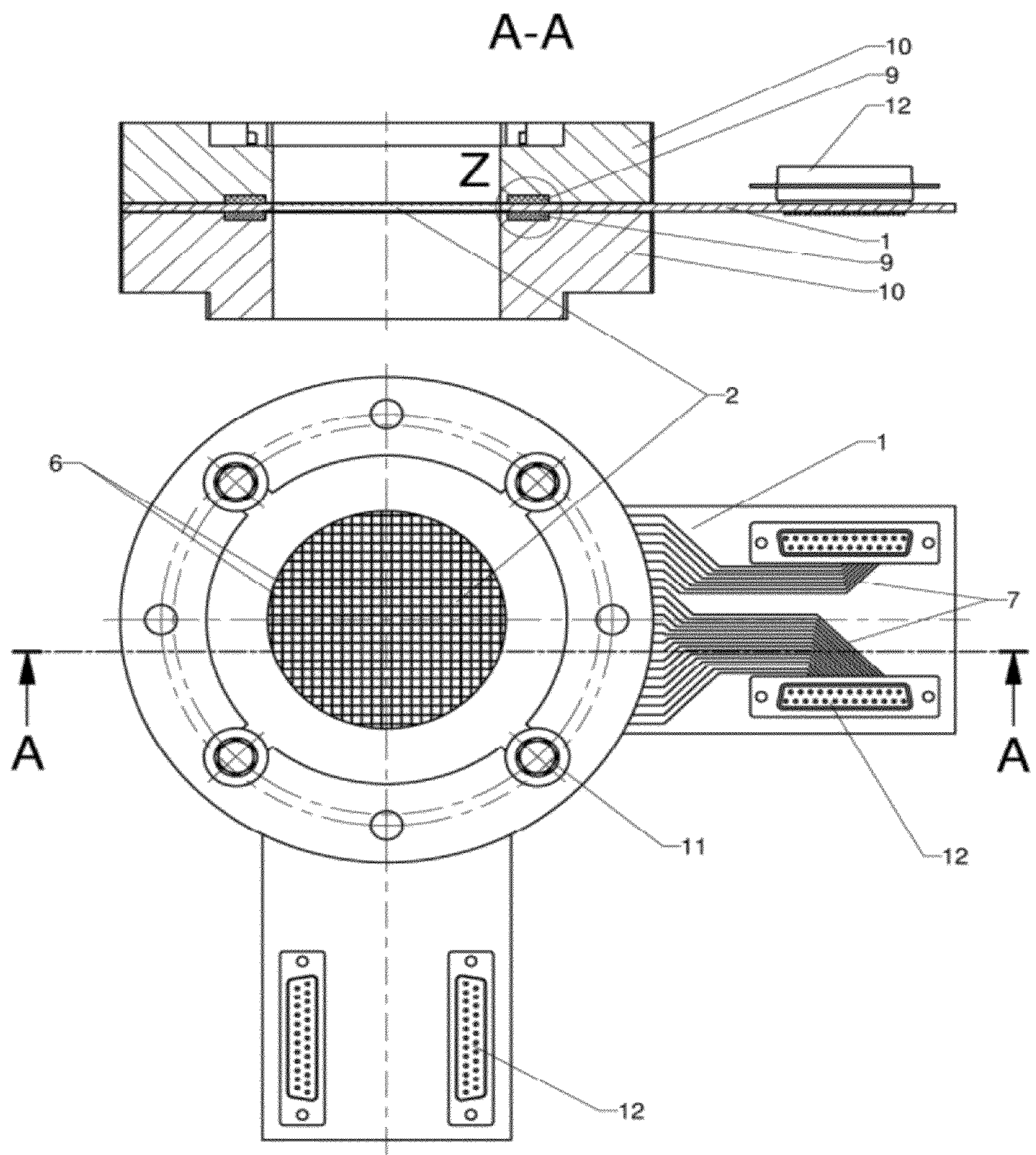
FIG. 2 shows a section and plan view of the grid sensor.
Figure 3:
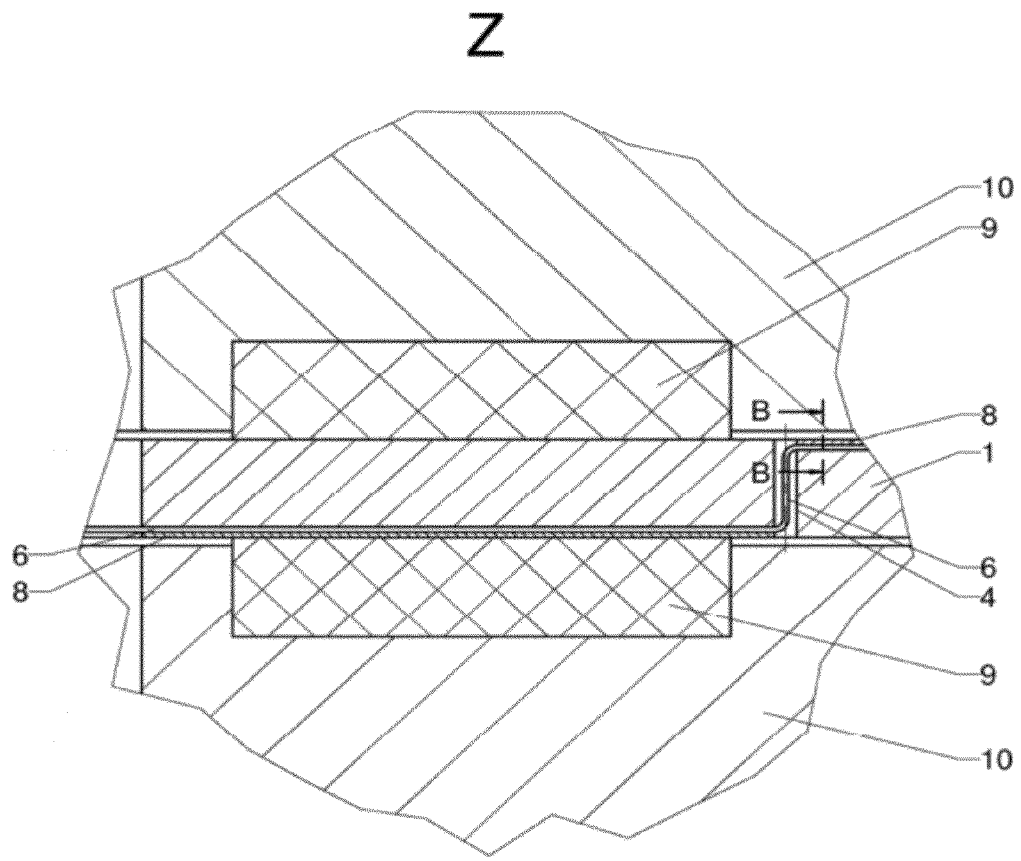
FIG. 3 shows the detail Z from the section as per FIG. 2.
Figure 4:
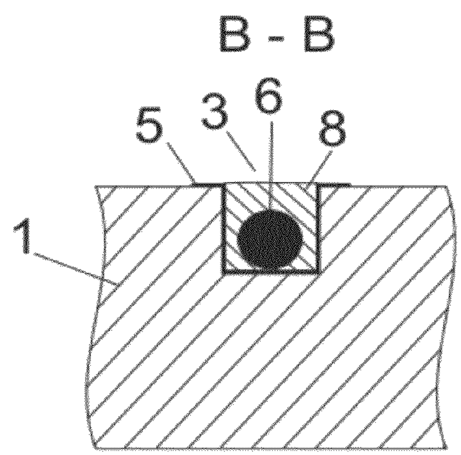
FIG. 4 shows the part section B-B from FIG. 3.

The grid sensor comprises a sensor board (1) with a dielectric surface. The sensor board can be a ceramic substrate, a metal plate coated by an abrasion-resistant insulation layer or a fiber-reinforced plastic board made of FR4, for example. The sensor board (1) comprises at least one cutout which corresponds to the measurement cross section (2) which is to be measured later. Channels (3) inserted into the base material by milling and having a depth of less than half the thickness of the sensor board (1) run outwardly from the edge of the free measurement cross section (2) in said sensor board (1). In the process, the channels (3) are arranged according to the desired geometry of the sensor grid. As illustrated in FIG. 1, it is conventional for wire electrodes (6) to be spanned in respectively two axially offset planes, wherein the wire electrodes (6) within one plane are preferably oriented parallel to one another and the wire electrodes (6) in different planes are oriented with respect to one another by an angle greater than 0°, preferably orthogonally in the case of two electrode planes. In order to fix a wire electrode (6), provision is made for respectively two channels (3) which respectively lie opposite each other at the measurement cross section (2) such that the wire electrode (6) spans the measurement cross section (2) in the desired position. Here, the channels (3) of the first sensor plane (excitation plane) are located on the one side of the sensor board (1) and the channels (3) of the second sensor plane (receiver plane) are located on the other side of the sensor board (1), wherein the wire electrodes (6) in one plane are arranged orthogonally to one another in respect of the other plane. At a distance from the edge of the free cross section (2), there is respectively one bore (4) in each channel (3) which creates a passage to the opposite side of the sensor board (1).The respective channel (3) on the opposite side of the sensor board (1) continues from this bore (4). The inner surfaces of the channels (3) and the bores (4) are coated by a thin metal layer (5), wherein care has to be taken that the individual channels are insulated from one another. A wire electrode (6) is spanned between respectively two opposing channels (3) lying on the same side of the sensor board (1) at the measurement cross section (2), which wire electrode is embedded in the corresponding channels (3), is led to the respective other side of the sensor board (1) through the bores (4) located in the channels (3) and is fixed in the channel (3) on both sides of the sensor board (1) by means of a conductive sealing compound (8), for example brazing or soft solder. Here, the seal with a conductive compound is designed such that the conductive sealing compound (8) located in the channel (3) in each case terminates flush with the upper edge of the sensor board (1) and in the process does not have a connection to one of the adjacent channels (3). Furthermore, in each case at least one of the metalized channels (3) of each wire electrode (6) is electrically connected to a cable connection point or plug connector (12) via a metal conductor track (7), which connector serves as the electrical connection of the sensor board (1) with processing electronics. The sensor board (1) is clamped between two clamping boards (10) by means of two flat sealing rings (9) made of dielectric material and placed on both sides. The two clamping boards (10) are clamped against each other by means of clamping screws (11) for applying the compression strength. Corresponding cutouts are provided in the sensor board (1) for leading the clamping screws (11) through the latter.

Using the same scheme of exciting transmission electrodes and measuring the electrical current at the receiver electrodes of such a grid it is also possible to measure distributions of other electrical variables, such as the electrical capacitance or impedance, or even non-electrical variables, by connecting the wire electrodes to solid state structures at the crossing points, the resistance value of which structures depending on a non-electrical physical variable of the surroundings.

The invention claimed is:

1. A grid sensor for two-dimensional measurement of electrical or non-electrical variables of a measurement cross section, essentially comprising:

a sensor board made of a dielectric base material with at least one measurement cross section, wire electrodes spanning the measurement cross section such that they span a grid with at least two parallel planes, wherein the first grid plane on the upper side of the sensor board comprises a set of wire electrodes which are preferably oriented in parallel and do not cross and the second grid plane on the lower side of the sensor board likewise comprises a set of wire electrodes which are oriented substantially in parallel and do not cross and the wire electrodes of the various planes are oriented with respect to each other by an angle greater than 0°, an electrically conductive connection between each wire electrode and an electric wire connection point or plug connector at the edge of the sensor board, characterized in that channels which are wider than the diameter of the wire electrodes and have a depth of less than half the thickness of the sensor board run outwardly from the edge of the measurement cross section in said sensor board, the channels are coated by a metal layer, the wire electrodes are inserted into the periphery of the measurement cross section with the two ends of said electrode each in one of the opposite channels and said electrodes are fixed in the channels by means of a conductive sealing compound such as brazing solder or soft solder, in each channel the conductive sealing compound terminates in a planar fashion with the upper side of the sensor board, the sensor board is clamped between two clamping plates and respectively one flat sealing ring, inserted on the upper and lower side, by means of a few clamping screws arranged on the edge of the sensor.

2. The grid sensor as claimed in claim 1, characterized in that outside of the flat sealing ring, at a distance of at least a few millimeters from the edge of the measurement cross section, bores are introduced within the channels and create a passage to the respective other side of the sensor board, on the opposite side of the sensor board with respect to the channels, provision is made in the sensor board for additional channels which originate at the bores, have a length of a few millimeters and are continued in said sensor board, the bores and channels are coated by a metal layer, the wire electrodes spanned across the measurement cross section are led to the channels on the other side of the sensor board through the channels on the one side of the sensor board and the bores.

3. The grid sensor as claimed in claim 1, characterized in that channels of various depths are worked into the sensor board and a grid with more than two planes is implemented by means of the wire electrodes which are fixed in these channels by an electrically conductive sealing compound and which span across the measurement cross section.

4. The grid sensor as claimed in claim 1, characterized in that a plurality of sensor boards are clamped and fixed by means of inserted flat sealing rings and possibly additional spacing plates between two clamping plates are clamped and fixed by means of a few clamping screws arranged on the edge of the sensor, and thus can be used as a multi-plane grid sensor.

5. The grid sensor as claimed in claim 1, characterized in that the two clamping plates have a recess which prevents the inserted flat sealing rings from being pressed into the measurement cross section when being pressed on.

6. The grid sensor as claimed in claim 1, characterized in that the flat sealing rings are replaced by O or X rings.

* * * * *